United States Patent
Gellman et al.

(10) Patent No.: US 7,651,529 B2
(45) Date of Patent: Jan. 26, 2010

(54) STRICTURE RETRACTOR

(75) Inventors: Barry N. Gellman, N. Easton, MA (US); Jozef Slanda, Milford, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 595 days.

(21) Appl. No.: 10/434,756

(22) Filed: May 9, 2003

(65) Prior Publication Data
US 2004/0225372 A1 Nov. 11, 2004

(51) Int. Cl.
*A61F 2/04* (2006.01)
(52) U.S. Cl. .................................. 623/23.66; 606/198
(58) Field of Classification Search ............ 606/8, 606/191, 108, 109, 198; 623/23.07, 23.66, 623/23.7; 604/104–109, 264, 96.01, 174, 604/175, 177, 179; 411/15, 21, 24–27, 36, 411/75–77
See application file for complete search history.

(56) References Cited

U.S. PATENT DOCUMENTS

| | | | |
|---|---|---|---|
| 3,527,226 A | | 9/1970 | Hakim et al. |
| 3,626,950 A | * | 12/1971 | Schulte .................. 604/268 |
| 3,657,744 A | | 4/1972 | Ersek |
| 3,923,066 A | | 12/1975 | Francisoud et al. |
| 3,938,529 A | | 2/1976 | Gibbons |
| 3,946,741 A | * | 3/1976 | Adair .................... 604/105 |
| 4,154,242 A | | 5/1979 | Termanini |
| 4,156,067 A | | 5/1979 | Gould |
| 4,240,434 A | | 12/1980 | Newkirk |
| 4,307,723 A | | 12/1981 | Finney |
| 4,350,161 A | | 9/1982 | Davis, Jr. ............... 128/349 |
| 4,423,725 A | | 1/1984 | Baran et al. |
| 4,432,757 A | | 2/1984 | Davis, Jr. ............... 604/99 |
| 4,585,000 A | * | 4/1986 | Hershenson ............ 604/109 |
| 4,627,838 A | | 12/1986 | Cross et al. |
| 4,655,771 A | | 4/1987 | Wallsten |
| 4,660,560 A | | 4/1987 | Klein |
| 4,713,049 A | | 12/1987 | Carter |
| 4,732,152 A | | 3/1988 | Wallsten et al. |
| 4,768,507 A | | 9/1988 | Fischell et al. |
| 4,771,773 A | | 9/1988 | Kropf et al. |
| 4,813,429 A | | 3/1989 | Eshel et al. |

(Continued)

FOREIGN PATENT DOCUMENTS

EP 0 274 846 7/1988

(Continued)

OTHER PUBLICATIONS 4-page Int'l Search Report from PCT/US2004/013782.

(Continued)

*Primary Examiner*—Anhtuan T Nguyen
*Assistant Examiner*—Tuan V Nguyen

(57) ABSTRACT

The invention includes a system and method for reducing the approximation of wound edges of a stricture that affects a cross-sectional area of a lumen in a mammal. The system includes a body defining a passageway for fluid flow. The body is positionable in the lumen. The system also includes a separating device disposed relative to the body. The separating device can adjust the cross-sectional area of the lumen to reduce approximation of the plurality of wound edges of the stricture. Moreover, the separating device facilitates fluid flow through the passageway of the body.

24 Claims, 17 Drawing Sheets

U.S. PATENT DOCUMENTS

| | | |
|---|---|---|
| 4,895,566 A | 1/1990 | Lee |
| 4,931,037 A | 6/1990 | Wetterman |
| 4,932,938 A | 6/1990 | Goldberg et al. |
| 4,954,126 A | 9/1990 | Wallsten |
| 4,955,859 A | 9/1990 | Zilber |
| 4,973,301 A | 11/1990 | Nissenkorn |
| 4,990,155 A | 2/1991 | Wilkoff |
| 4,994,066 A | 2/1991 | Voss |
| 4,995,868 A | 2/1991 | Brazier |
| 5,026,377 A | 6/1991 | Burton et al. |
| 5,037,427 A | 8/1991 | Harada et al. |
| 5,041,092 A | 8/1991 | Barwick |
| 5,061,275 A | 10/1991 | Wallsten et al. |
| 5,078,720 A | 1/1992 | Burton et al. |
| 5,087,252 A | 2/1992 | Denard |
| 5,116,309 A | 5/1992 | Coll |
| 5,122,154 A | 6/1992 | Rhodes |
| 5,147,370 A | 9/1992 | McNamara et al. |
| 5,160,341 A | 11/1992 | Brenneman et al. |
| 5,167,614 A | 12/1992 | Tessmann et al. |
| 5,176,625 A | 1/1993 | Brisson |
| 5,176,626 A | 1/1993 | Soehendra |
| 5,183,085 A | 2/1993 | Timmermans |
| 5,195,989 A | 3/1993 | Euteneuer |
| 5,217,451 A | 6/1993 | Freitas |
| 5,220,927 A | 6/1993 | Astrahan et al. |
| 5,222,971 A | 6/1993 | Willard et al. |
| 5,224,953 A | 7/1993 | Morgentaler |
| 5,234,456 A | 8/1993 | Silvestrini |
| 5,246,445 A | 9/1993 | Yachia et al. |
| 5,258,020 A | 11/1993 | Froix |
| 5,269,802 A | 12/1993 | Garber |
| 5,279,565 A * | 1/1994 | Klein et al. ................. 604/105 |
| 5,282,784 A | 2/1994 | Willard |
| 5,282,823 A | 2/1994 | Schwartz et al. |
| 5,286,254 A | 2/1994 | Shapland et al. |
| 5,292,315 A | 3/1994 | Euteneuer |
| 5,300,022 A | 4/1994 | Klapper et al. |
| 5,304,121 A | 4/1994 | Sahatjian |
| 5,316,016 A | 5/1994 | Adams et al. |
| 5,322,501 A | 6/1994 | Mahmud-Durrani |
| 5,342,348 A | 8/1994 | Kaplan |
| 5,344,395 A | 9/1994 | Whalen et al. |
| 5,352,198 A | 10/1994 | Goldenberg et al. |
| 5,354,263 A | 10/1994 | Coll |
| 5,354,309 A | 10/1994 | Schnepp-Pesch et al. |
| 5,356,423 A | 10/1994 | Tihon et al. |
| 5,364,340 A | 11/1994 | Coll |
| 5,372,600 A | 12/1994 | Beyar et al. |
| 5,383,928 A | 1/1995 | Scott et al. |
| 5,391,196 A | 2/1995 | Devonec |
| 5,409,460 A | 4/1995 | Krumme |
| 5,419,760 A | 5/1995 | Narciso, Jr. |
| 5,421,955 A | 6/1995 | Lau et al. |
| 5,429,634 A | 7/1995 | Narciso, Jr. |
| 5,441,515 A | 8/1995 | Khosravi et al. |
| 5,441,516 A | 8/1995 | Wang et al. |
| 5,456,667 A | 10/1995 | Ham et al. |
| 5,464,650 A | 11/1995 | Berg et al. |
| 5,496,277 A | 3/1996 | Termin et al. |
| 5,499,994 A | 3/1996 | Tihon et al. |
| 5,514,176 A | 5/1996 | Bosley, Jr. |
| 5,514,178 A | 5/1996 | Torchio |
| 5,514,669 A | 5/1996 | Selman |
| 5,520,697 A | 5/1996 | Lindenberg et al. |
| 5,536,242 A | 7/1996 | Willard et al. |
| 5,540,701 A | 7/1996 | Sharkey et al. ............... 606/153 |
| 5,545,208 A | 8/1996 | Wolff et al. |
| 5,545,211 A | 8/1996 | An et al. ........................ 623/1 |
| 5,549,559 A | 8/1996 | Eshel |
| 5,549,595 A | 8/1996 | Freitas |
| 5,554,181 A | 9/1996 | Das |
| 5,556,413 A | 9/1996 | Lam |
| 5,562,622 A | 10/1996 | Tihon |
| 5,584,872 A | 12/1996 | LaFontaine et al. |
| 5,588,965 A | 12/1996 | Burton et al. |
| 5,593,403 A | 1/1997 | Buscemi |
| 5,599,306 A | 2/1997 | Klein et al. |
| 5,601,591 A | 2/1997 | Edwards et al. |
| 5,609,583 A | 3/1997 | Hakki et al. |
| 5,609,629 A | 3/1997 | Fearnot et al. |
| 5,618,299 A | 4/1997 | Khosravi et al. |
| 5,626,562 A | 5/1997 | Castro |
| 5,653,684 A | 8/1997 | Laptewicz |
| 5,667,486 A | 9/1997 | Mikulich et al. |
| 5,667,490 A | 9/1997 | Keith et al. |
| 5,674,241 A | 10/1997 | Bley et al. |
| 5,676,693 A | 10/1997 | LaFontaine |
| 5,702,361 A | 12/1997 | Evans et al. |
| 5,702,419 A | 12/1997 | Berry et al. |
| 5,707,386 A | 1/1998 | Schnepp-Pesch et al. |
| 5,723,003 A | 3/1998 | Winston et al. |
| 5,725,549 A | 3/1998 | Lam |
| 5,733,303 A | 3/1998 | Israel et al. |
| 5,738,654 A | 4/1998 | Tihon |
| 5,766,209 A | 6/1998 | Devonec |
| 5,766,238 A | 6/1998 | Lau et al. |
| 5,772,668 A | 6/1998 | Summers et al. |
| 5,776,142 A | 7/1998 | Gunderson |
| 5,776,161 A | 7/1998 | Globerman |
| 5,782,838 A | 7/1998 | Beyar et al. |
| 5,792,400 A | 8/1998 | Talja et al. |
| 5,797,952 A | 8/1998 | Klein |
| 5,817,102 A | 10/1998 | Johnson et al. |
| 5,824,037 A | 10/1998 | Bogarty et al. |
| 5,824,038 A | 10/1998 | Wall |
| 5,830,179 A | 11/1998 | Mikus et al. |
| 5,833,707 A | 11/1998 | McIntyre et al. |
| 5,843,103 A | 12/1998 | Wulfman |
| 5,865,815 A | 2/1999 | Tihon |
| 5,876,417 A | 3/1999 | Devonec et al. |
| 5,876,445 A | 3/1999 | Andersen et al. |
| 5,888,201 A | 3/1999 | Stinson et al. |
| 5,902,317 A | 5/1999 | Kleshinski et al. .......... 606/198 |
| 5,902,328 A | 5/1999 | LaFontaine et al. |
| 5,911,752 A | 6/1999 | Dustrude et al. |
| 5,916,195 A | 6/1999 | Eshel et al. |
| 5,916,227 A | 6/1999 | Keith et al. |
| 5,928,208 A | 7/1999 | Chu et al. |
| 5,928,217 A | 7/1999 | Mikus et al. |
| 5,938,670 A | 8/1999 | Keith et al. |
| 5,957,929 A | 9/1999 | Brenneman |
| 5,964,732 A | 10/1999 | Willard |
| 5,964,744 A | 10/1999 | Balbierz et al. |
| 5,964,771 A | 10/1999 | Beyar et al. |
| 5,976,165 A | 11/1999 | Ball et al. |
| 5,980,550 A | 11/1999 | Eder et al. |
| 6,001,117 A | 12/1999 | Huxel et al. |
| 6,004,328 A | 12/1999 | Solar |
| 6,017,977 A | 1/2000 | Evans et al. |
| 6,019,779 A | 2/2000 | Thorud et al. |
| 6,022,312 A | 2/2000 | Chaussy et al. |
| 6,023,638 A | 2/2000 | Swanson |
| 6,024,763 A | 2/2000 | Lenker et al. |
| 6,033,413 A | 3/2000 | Mikus et al. |
| 6,042,606 A | 3/2000 | Frantzen |
| 6,047,218 A | 4/2000 | Whayne et al. |
| 6,050,949 A | 4/2000 | White et al. |
| 6,053,900 A | 4/2000 | Brown et al. |
| 6,066,167 A | 5/2000 | Lau et al. |
| 6,066,168 A | 5/2000 | Lau et al. |
| 6,090,103 A | 7/2000 | Hakky et al. |
| 6,090,115 A | 7/2000 | Beyar et al. |
| 6,113,594 A | 9/2000 | Savage |

| | | |
|---|---|---|
| 6,113,597 A | 9/2000 | Eggers et al. |
| 6,119,697 A | 9/2000 | Engel et al. |
| 6,126,667 A | 10/2000 | Barry et al. |
| 6,132,460 A | 10/2000 | Thompson |
| 6,132,461 A | 10/2000 | Thompson |
| 6,139,536 A | 10/2000 | Mikus et al. |
| 6,146,416 A | 11/2000 | Andersen et al. |
| 6,152,919 A | 11/2000 | Hakky |
| 6,156,064 A | 12/2000 | Chouinard |
| 6,162,215 A | 12/2000 | Feng |
| 6,162,231 A | 12/2000 | Mikus et al. |
| 6,165,210 A | 12/2000 | Lau et al. |
| 6,174,305 B1 | 1/2001 | Mikus et al. |
| 6,176,875 B1 | 1/2001 | Lenker et al. |
| 6,179,868 B1 | 1/2001 | Burpee et al. |
| 6,187,015 B1 | 2/2001 | Brenneman |
| 6,214,037 B1 | 4/2001 | Mitchell et al. |
| 6,221,081 B1 | 4/2001 | Mikus et al. |
| 6,238,430 B1 | 5/2001 | Klumb et al. |
| 6,245,103 B1 | 6/2001 | Stinson ............... 623/1.22 |
| 6,254,628 B1 | 7/2001 | Wallace et al. |
| 6,258,115 B1 | 7/2001 | Dubrul ............... 606/200 |
| 6,299,636 B1 | 10/2001 | Schmitt et al. ............ 623/1.2 |
| 6,334,866 B1 | 1/2002 | Wall |
| 6,355,061 B1 | 3/2002 | Quiachon et al. |
| 6,355,070 B1 | 3/2002 | Andersen et al. ........... 623/23.7 |
| 6,371,979 B1 | 4/2002 | Beyar et al. |
| 6,451,025 B1 | 9/2002 | Jervis |
| 6,494,879 B2 | 12/2002 | Lennox et al. |
| 6,494,908 B1 | 12/2002 | Huxel et al. |
| 6,589,214 B2 * | 7/2003 | McGuckin et al. ........ 604/175 |
| 6,855,126 B2 * | 2/2005 | Flinchbaugh ............ 604/106 |
| 6,929,621 B2 * | 8/2005 | Whitmore et al. .......... 604/109 |
| 2002/0055787 A1 | 5/2002 | Lennox et al. |
| 2002/0107540 A1 | 8/2002 | Whalen et al. |
| 2002/0177904 A1 | 11/2002 | Huxel et al. |
| 2003/0040803 A1 | 2/2003 | Rioux et al. |
| 2003/0045924 A1 | 3/2003 | Datta et al. |
| 2004/0181235 A1 * | 9/2004 | Daignault et al. ............ 606/108 |

FOREIGN PATENT DOCUMENTS

| | | |
|---|---|---|
| EP | 0 341 988 | 11/1989 |
| EP | 0 543 309 A1 | 11/1992 |
| EP | 0 935 977 A3 | 8/1999 |
| FR | 2 661 603 | 5/1990 |
| WO | WO 80/01460 | 7/1980 |
| WO | WO 89/03232 | 4/1989 |
| WO | WO 91/16005 | 10/1991 |
| WO | WO 95/03848 | 2/1995 |
| WO | WO 96/23449 | 8/1996 |
| WO | WO 99/23952 | 5/1999 |
| WO | WO 00/15130 | 3/2000 |
| WO | WO 00/16005 | 3/2000 |
| WO | WO 00/18907 | 4/2000 |
| WO | WO 00/19926 | 4/2000 |
| WO | WO 00/21462 | 4/2000 |
| WO | WO 00/45744 | 8/2000 |
| WO | WO 00/51521 | 9/2000 |
| WO | WO 00/56247 | 9/2000 |
| WO | WO 00/59558 | 10/2000 |
| WO | WO 00/69367 | 11/2000 |
| WO | WO 00/69498 | 11/2000 |
| WO | WO 00/76425 | 12/2000 |
| WO | WO 01/10345 | 2/2001 |
| WO | WO 01/56629 | 8/2001 |
| WO | WO 02/05841 | 8/2002 |

OTHER PUBLICATIONS 14-page Written Opinion from PCT/US2004/013782.
Andrich et al.; "Surgery for urethral stricture disease" *Contemporary Urology*, Dec. 2001, pp. 32-34, 39-42, and 44.
Duerig et al.; "An Overview of Superelastic Stent Design"; © 2000 Isis Medical Media Ltd.; (pp. 235-246).
PCT International Search Report for PCT/US02/14895.

* cited by examiner

STRICTURE RETRACTOR

TECHNICAL FIELD

This invention generally relates to strictures and, more specifically, methods and devices to reduce approximation of wound edges of a stricture in a lumen of a body.

BACKGROUND INFORMATION

Suffering an injury is often painful and upsetting to the injured party. The body typically responds in several fashions, often dependent upon the type and severity of the injury. One such response is the production of scar tissue, whose growth may impede other parts of the body. The scar tissue's growth can lead to other problems within the body. For example, scar tissue can form around and/or affect a lumen of the body, thereby potentially narrowing the lumen. This narrowing of the lumen, also called a stricture, typically reduces the amount of fluid that can flow through the lumen.

An example of a lumen that a stricture can affect is the urethra. The male urethra is generally a tubular passageway extending from the bladder to the end of the penis. As urine travels from the bladder and out of the body, the urine passes through the urethra. A stricture, however, narrows the urethra. This narrowing of the urethra (i.e., lumen) can impede fluid flow (e.g., urine) through the urethra, cause pain during use of the urethra, and/or require medical intervention to expand or stretch the obstruction.

A trauma to the urethra or surrounding areas is an example of an event that can cause the formation of a stricture. A trauma can be the result of an external injury, such as a straddle injury (e.g., falling onto a bicycle frame). Pelvic fractures, which can occur as a result of an automobile accident, can also lead to strictures of the urethra. Surgical procedures involving the urethra can cause stricture formation. Other causes of a urethral stricture include an infection, such as gonorrhea, or inflammation of an area of the urethra.

To treat a stricture, medical professionals (e.g., doctors, nurses, hospital employees, or people with medical training) often have several options. One option is a procedure called dilation. Dilation is performed in the medical professional's office and involves stretching of the stricture using progressively larger dilators. Another option, which medical professionals perform in the operating room using an endoscopic instrument, is called internal urethrotomy. Internal urethrotomy involves an internal incision of the stricture through the penis to open the stricture. Thus, the medical professional typically cuts the stricture to remove the narrowing of the urethra.

After the surgical incision through the stricture, the stricture's wound edges heal. If left unattended, the stricture's wound edges can heal together, likely resulting in a larger stricture than present before the surgical incision. Thus, the surgery's objective of removing the narrowing of the urethra may be met temporarily, but the healing of the stricture can narrow the urethra even further.

The medical professional typically places a catheter into the urethra after the surgical incision is made. The catheter typically keeps the urethra opened after the surgery until the catheter is removed (after a certain period of time). In addition to helping prevent subsequent recurrence of a stricture, patency of the urethra is important for several reasons, such as to aid in the healing of the urethra, for the drainage of urine, and to enable vascular flow through the urethra. One such type of catheter that a medical professional inserts is a Foley catheter.

The technique of using a catheter to maintain urethral patency, however, is subject to several drawbacks. First, the catheter that the medical professionals insert to maintain the proper opening of the urethra has a fixed diameter. Thus, because catheters are typically limited to a fixed diameter, wound edges can form up to the diameter of the catheter. Moreover, dilation devices, such as balloons, can hinder or prevent blood or other bodily fluids from flowing through the urethra because the passageway or a large portion of the passageway is typically blocked by the dilation device. Catheters may also suffer from this drawback, as their diameter can limit the amount of fluid that can flow in and out of the urethra when attempting to prevent wound edges from approximating.

Although described above with a urethra, a stricture may form around any other type of lumen, such as a person's esophagus. Further, the problems described above also apply to these other types of lumens. Thus, there is a need to reduce the approximation of wound edges of a stricture while not preventing fluid flow through the lumen.

SUMMARY OF THE INVENTION

The invention enables fluid flow through a lumen that is narrowed by a stricture while also reducing the approximation of wound edges of the stricture.

In one aspect, the invention includes a system for reducing the approximation of wound edges of a stricture that affects a cross-sectional area of a lumen in a mammal. The system, or stricture retracting system, includes a body defining a passageway for fluid flow. The body is positionable in the lumen. The system also includes a separating device disposed relative to the body. The separating device can adjust the cross-sectional area of the lumen to reduce approximation of the plurality of wound edges of the stricture. Moreover, the separating device facilitates fluid flow through the passageway of the body.

The separating device can include wings and can be connected to or coupled to the body. Additionally, the system can also include an actuating mechanism that communicates with the separating device. The actuating mechanism can communicate with the separating device for disposing the separating device relative to the body for the adjusting of the cross-sectional area of the lumen. In one embodiment, the actuating mechanism is a spring that is connected to the separating device to dispose the separating device relative to the body.

Moreover, the actuating mechanism can include a mechanical device, a pneumatic device, a hydraulic device, or an electronic device. The actuating mechanism can also include a slide cam or a screw cam. Further, the body can include one or more separating device slits for disposing the separating device. The body can also include a control ring that enables adjustment of the cross-sectional area of the lumen.

In another aspect, the invention includes a flexible member that is positionable in a lumen and a controller. The controller can adjust the pressure of the flexible member to alter the cross-sectional area of the lumen. This reduction in the cross-sectional area of the lumen reduces approximation of wound edges of the stricture. Moreover, the adjustment of the pressure facilitates fluid flow through the lumen.

In one embodiment, the controller includes a valve. The controller can also include an electrical controller connected to the flexible member for adjusting the pressure of the flexible member. Additionally, the flexible member can be hydraulic or pneumatic and can be made from a compliant material or a semi-compliant material.

In yet another aspect, a system for reducing approximation of wound edges of a stricture that affects a cross-sectional area of a lumen in a mammal includes means for adjusting the cross-sectional area of the lumen. The adjustment of the cross-sectional area reduces approximation of wound edges of a stricture. Moreover, the system includes means for facilitating fluid flow through the lumen after adjusting the cross-sectional area of the lumen.

In another aspect, the invention includes a method for reducing approximation of wound edges of a stricture. The method includes the step of inserting a body defining a passageway into the lumen. The method also includes the step of causing a separating device disposed relative to the body to adjust the cross-sectional area of the lumen for reducing approximation of the wound edges of the stricture. The method additionally includes facilitating fluid flow through the passageway of the body of the lumen.

The method can include employing an actuating mechanism to cause the separating device to adjust the cross-sectional area of the lumen. This can include translating a cam device or mechanically rotating a cam device. Further, the amount of cross-sectional area adjustment can also be adjustable.

BRIEF DESCRIPTION OF DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

DETAILED DESCRIPTION

Figure 1:
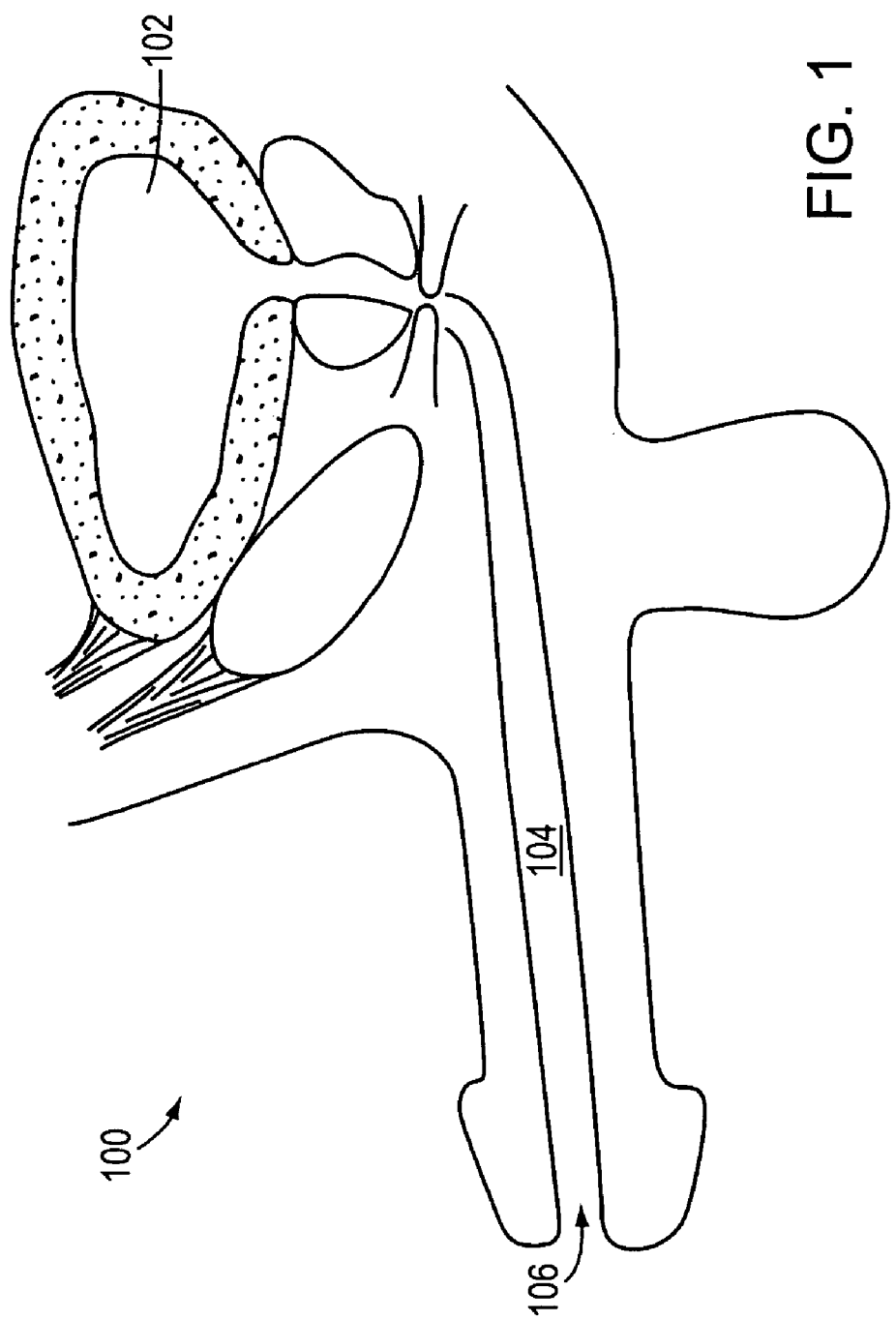
FIG. 1 is an embodiment of a schematic view of a male urinary system.

FIG. 1 shows a male urinary system 100, which includes a bladder 102 and a urethra 104. The male urethra 104 is generally a tubular passageway extending from the bladder 102 to the meatus 106 of the penis. As urine travels from the bladder 102 and out of the body, the urine passes through four sections of the urethra 104, referred to as the prostatic urethra, the membranous urethra, the bulbar urethra, and the pendulous or distal urethra. Surrounding the prostatic urethra and below the bladder 102 is a prostate gland 108, which, among other functions, produces the fluid in semen.

Figure 2A:
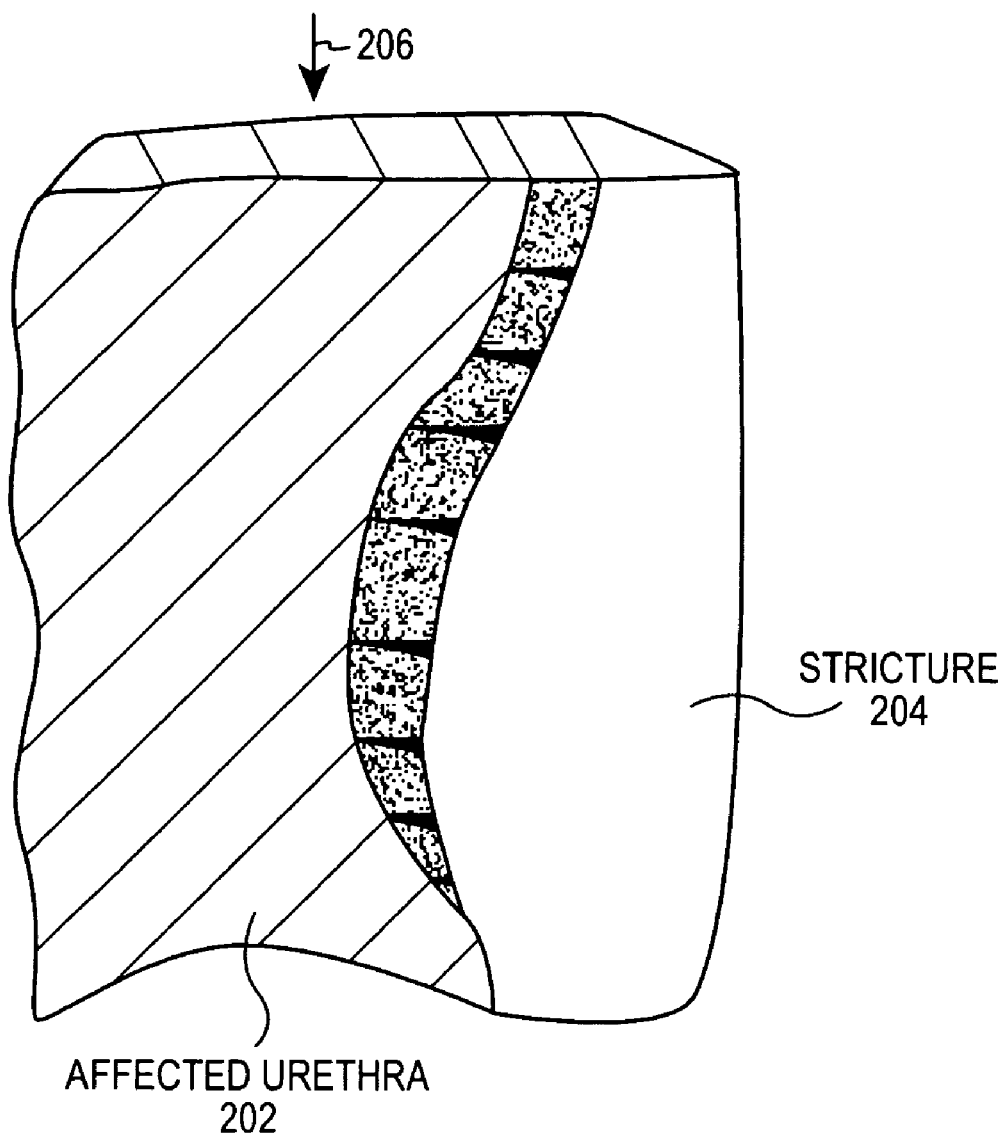
FIG. 2A is an embodiment of a perspective view of a stricture affecting a urethra.

FIG. 2A shows a perspective view of a portion of the urethra that is affected by a stricture 204. The affected urethra 202 is narrowed by the stricture 204. Urine 206 flows through the affected urethra 202. The stricture 204, however, decreases the volume of urine 206 that can pass through the affected urethra 202 at any given time because of the narrowing of the affected urethra 202. Moreover, the stricture 204 can become so large that the stricture 204 substantially blocks urine flow 206 through the affected urethra 202.

Figure 2B:
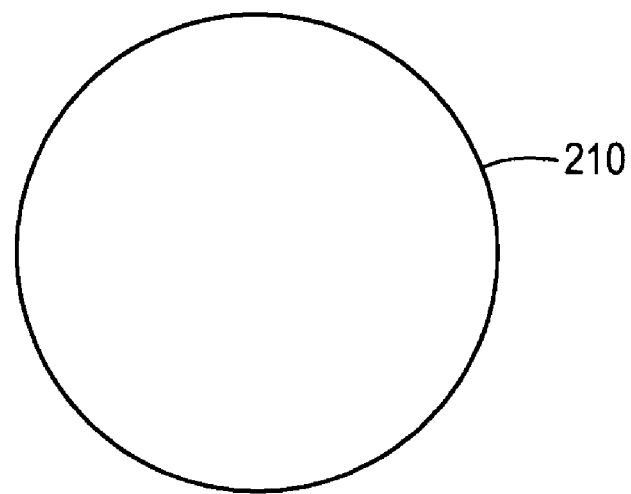
FIG. 2B is an embodiment of a cross-sectional view of a urethra not affected by a stricture.
Figure 2C:
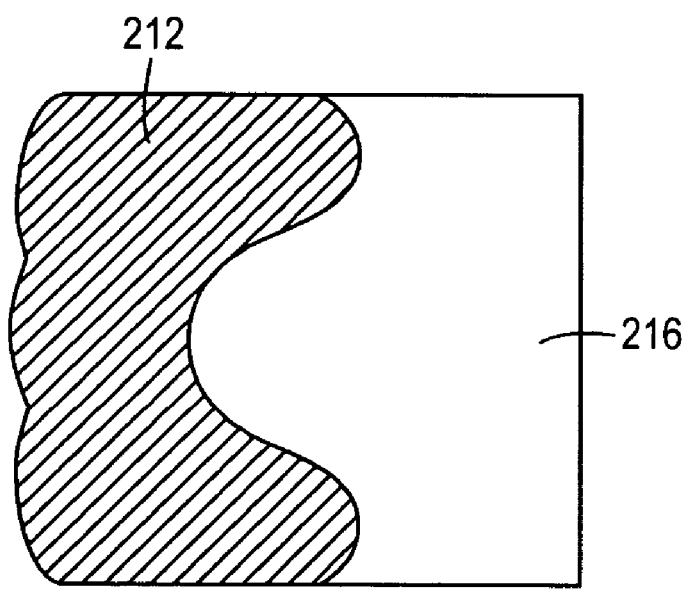
FIG. 2C is an embodiment of a cross-sectional view of a urethra affected by a stricture.

FIG. 2B refers to a cross-sectional view of a urethra not affected by a stricture. The unaffected urethra 104 (i.e., all or a portion of the urethra 104) can have an initial, circular cross-sectional area 210. FIG. 2C is a cross-sectional view of the urethra 202 narrowed by the stricture 204. The cross-sectional area 212 of the affected urethra 202 is less than the initial cross-sectional area 210. Moreover, the amount of reduction in the cross-sectional area 212 of the affected urethra 202 relative to the initial cross-sectional area 210 varies depending on the stricture 204. Additionally, the stricture 204 affecting the urethra 202 has an initial cross-sectional area 216.

Figure 2D:
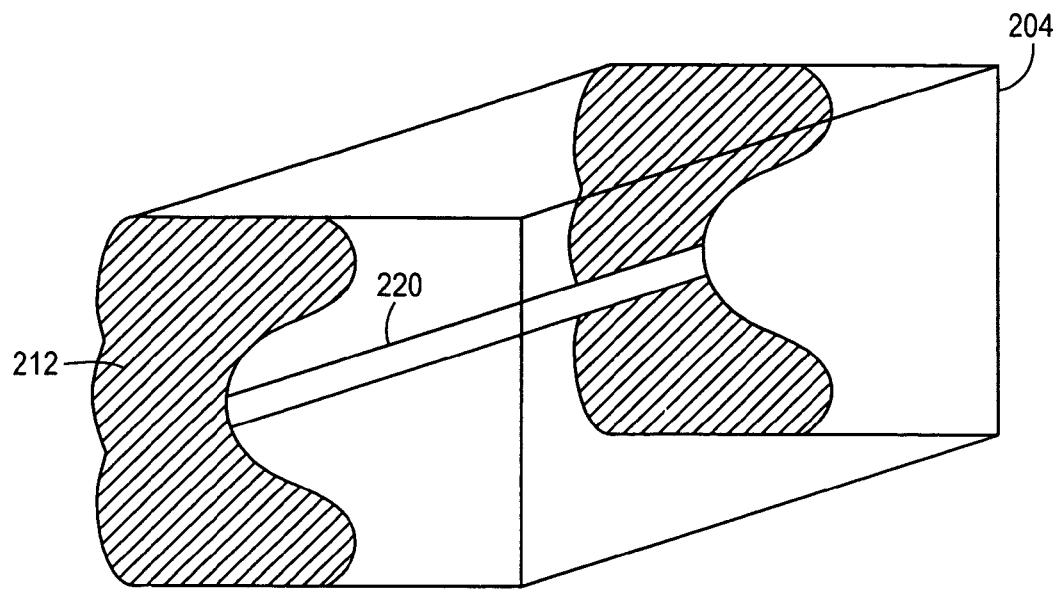
FIG. 2D is an embodiment of a perspective view of a surgical incision made through the stricture.

Referring to FIG. 2D, to reduce the narrowing of the affected urethra 202 and consequently relieve the pressure applied against the urethra 202, a medical professional makes a surgical incision 220 through the stricture. The incisions 220 can be made at a location at which the urethra is affected the greatest amount by the stricture 204. Moreover, in one embodiment the surgical incision 220 is made axially through the stricture 204. Further, the incision 220 has a depth equal to the depth of the stricture 204. Although described as being cut axially through the stricture, the incisions 220 may also be any direction and any size in order to relieve some of the effect that the stricture 204 has on the urethra 202.

Figure 2E:
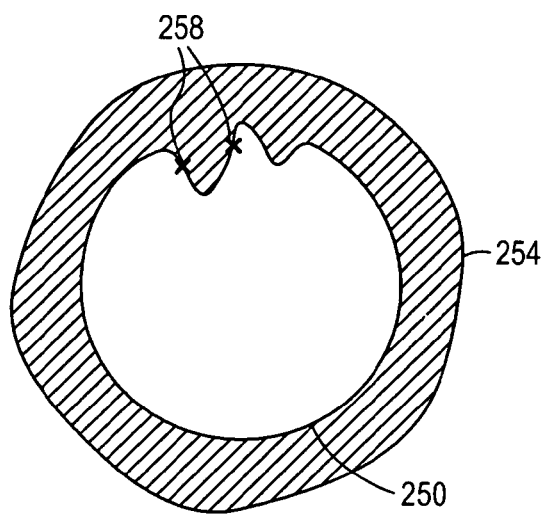
FIG. 2E is an embodiment of a cross-sectional view of the urethra affected by the stricture after the surgical incision of FIG. 2D is made.

Referring to FIG. 2E, once the medical professional cuts the stricture 204, the cross-sectional area 212 of the affected urethra 202 increases to a pressure-relieved cross-sectional area 250. Likewise, the initial cross-sectional area of the stricture 204 is reduced to an after-cut cross sectional area 254. Although shown with a particular cross-sectional area size and shape, the urethra 202, stricture 204, and/or cut 220 may have any size and any shaped cross-sectional area.

After the stricture 204 has been incised, wound edges 258 of the stricture 204 begin to heal together. Further, the healing of the stricture 204 can result in tougher, less vascular scar tissue (e.g., an epidermal layer). The stricture 204 may consequently contain more tissue mass. Moreover, the stricture 204 can become larger than before the cut 220 and again narrows the urethra 202 (e.g., such as the narrowing shown in FIG. 2A).

To reduce the approximation of the wound edges 258, the medical professional can insert a flexible member into the urethra 202. The medical professional can then adjust the pressure of the flexible member to keep the wound edges 258 apart while facilitating fluid flow through the urethra 202.

Figure 3:
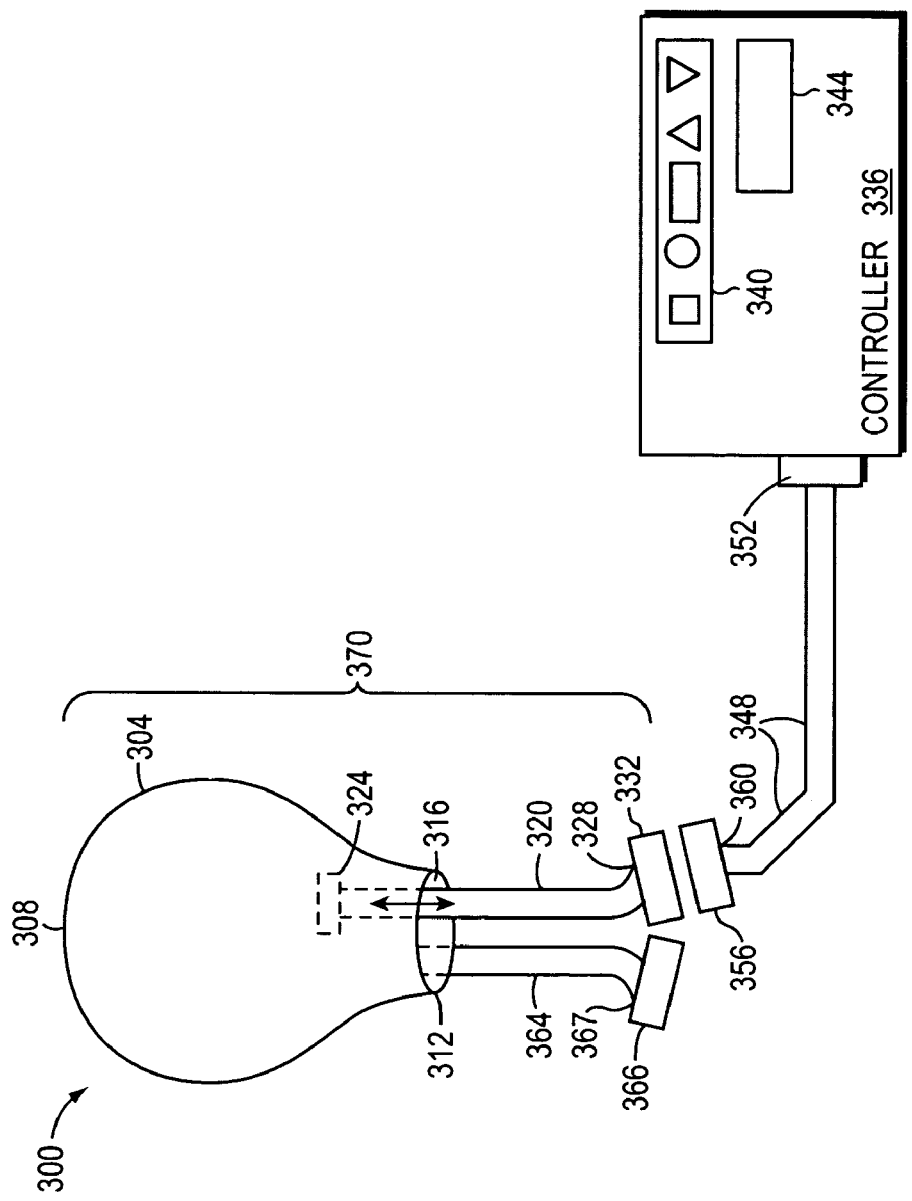
FIG. 3 is a block diagram of an embodiment of a stricture retracting system that provides therapeutic expansion of the urethra after the surgical incision through the stricture.

FIG. 3 shows an embodiment of a stricture retracting system 300 that provides therapeutic expansion of the urethra 202 after the surgical incision through the stricture 204. The system 300 includes a flexible member 304, which can be a balloon dilation device. The flexible member 304 can be constructed of any flexible material, such as a compliant material. Examples of compliant materials include silicone, urethane, and latex. Alternatively, the flexible member 304 can be made of a semi-compliant material, such as ethylene vinyl acetate or polyethene. Further, although described below as having a balloon-like shape and size, the flexible member 304 can have any shape or any size. Additionally, the flexible member 304 can be a pneumatically actuated device.

The flexible member 304 can also have an initial pressure that is set for insertion into the patient's urethra 202. The initial pressure of the flexible member 304 can also be set to a predetermined amount before delivery to the user of the flexible member 304. The user can additionally set the initial pressure before its insertion into the urethra 202. Thus, after the surgical cut 220 of the stricture 204, the user can insert the flexible member 304 into the urethra 202, which subsequently increases the pressure of the flexible member 304 to keep the wound edges 258 of the stricture 204 apart.

Moreover, the flexible member 304 has a distal end 308 which is inserted into the patient before the rest of the flexible member 304 and a proximal end 312. Although the flexible member 304 is shown with the portion of its body near the distal end 308 having a larger cross-sectional area than the cross-sectional area of a portion of the flexible member 304 near the proximal end 312, any portion of the flexible member 304 can be any size. The proximal end 312 of the flexible member 304 can include an opening 316 that can be used to adjust the pressure of the flexible member 304. The opening 316 can be adjustable so that a medical professional can open and close the opening 316. Moreover, the amount that the medical professional opens and closes the opening 316 can also be adjustable. For example, the medical professional can open the aperture 316 slightly to decrease the pressure of the flexible member 304 slightly.

Further, the flexible member 304 can include a flexible member line 320. The flexible member line 320 is connected to (e.g., attached to, passing through, or terminating at) the opening 316 so that the flexible member line 320 can adjust the pressure of the flexible member 304. The flexible member line 320 can be rigid or flexible. Examples of materials that the flexible member line 320 can be made with include thermoplastic, thermoset, metal, and composite materials. In one embodiment, the flexible member line 320 is secured inside the proximal end 312 of the flexible member 304 (e.g., through the opening 316). For example, the flexible member line 320 can be secured to the flexible member 304 with a fastening member 324, such as with tape, glue, a staple, or velcro. Moreover, a user can increase the length of the flexible member line 320 by pulling its proximate end 328 (i.e., the end furthest away from the opening 316 of the flexible member 304) in a direction away from the opening 316. Likewise, a user can also decrease the length of the flexible member line 320 by pushing its proximate end 328 in a direction towards the opening 316.

In yet other embodiments, a medical professional can adjust the shape of the flexible member line 320 for different scenarios. For instance, if a medical professional determines that the size and/or shape of the flexible member line 320 needs to be altered after insertion of the flexible member 304 into the urethra 202, the medical professional can choose a first flexible member line made from thermoplastic. Thus, when the medical professional determines that the first flexible member line needs adjustment, the medical professional can heat the first flexible member line to shape the flexible member line for its use. Moreover, the medical professional can choose a flexible member line 320 made from, for example, thermoplastic to facilitate recycling of the flexible member line 320.

The medical professional can additionally determine that the flexible member line 320 has to be consistent and stable, such as during exposure to heat. The medical professional can choose a flexible member line 320 made from a thermoset material. In another embodiment, the flexible member 304 enables the changing of the flexible member line 320. Thus, the medical professional can be able to unfasten the fastening member 324 and change the flexible member line 320 at any time before, during, or after the insertion of the flexible member 304 into the urethra 202.

The flexible member line 320 can also include a controller connector 332. The controller connector 332 enables the adjustment of pressure to the flexible member 304. The controller connector 332 can limit the type of devices that can be used to adjust the pressure to a device having a connector that mates with the controller connector 332.

The stricture retracting system 300 can additionally include a controller 336 to adjust the pressure of the flexible member 304. Examples of the controller 336 include a computer, a valve, and a pump. The controller 336 adjusts the pressure of the flexible member 304 to reduce approximation of at least some of the wound edges 258 of the stricture 204. Moreover, the controller 336 can also adjust the pressure to facilitate fluid flow through the urethra 202.

The controller 336 includes one or more control panels 340 enabling the medical professional to adjust the output of the controller 336. Each control panel 340 can include, for example, knobs, buttons, keys, and/or sliders to enable the medical professional to adjust the output of the controller 336. The control panel 340 can be a touch sensitive display having virtual knobs, buttons, keys and/or sliders. Further, an external computer (e.g., desktop computer or handheld computer) can control the controller 336. In particular, a software module executing on the computer can control the controller 336. The computer and/or the controller 336 can additionally be connected to a network, such as the Internet or World Wide Web. The network connection can enable the medical professional to remotely control the controller 336 via another computer.

Furthermore, the controller 336 can also include a display screen 344. The display screen 344 may display the settings of the controller 336 (e.g., number of pounds per square inch that the controller 336 is outputting, time settings, such as the length of time at which to output a predetermined number of pounds per square inch, program execution, etc.). The display screen 344 can be a touch sensitive panel having virtual buttons, knobs and settings.

The controller 336 also includes a controller line 348 for the delivery of the controller's output. For example, the controller 336 can provide air to inflate the flexible member 304. Like the flexible member line 320, the controller line 348 can be a rigid or flexible cable. Furthermore, the controller line 348 can be made with one or more of the materials described above for the flexible member line 320 (e.g., thermoplastic or composite materials). The user may also be able to adjust the length of the controller line 348 in a similar fashion as described above for the flexible member line 320 (e.g., by pushing the controller line 348 towards the controller 336 to shorten the line's length). Additionally, the controller line 348 can be secured to an output port 352 of the controller 336. Thus, the output port 352 enables a user to change the type of controller line 348 that delivers the output of the controller 336 (e.g., from a flexible controller line to a rigid controller line).

The controller line 348 also has a flexible member line connector 356 attached to its proximal end 360. The flexible member line connector 356 is a connector that mates with the controller connector 332. Moreover, once the connection is made between the two connectors 332, 356, the connectors may not be easily disconnected. For instance, the medical professional may not be able to disconnect the connectors 332, 356 until rotating each connector 332, 356 in opposite directions simultaneously. This security measure can prevent the connectors 332, 356 from disconnecting accidentally.

In one embodiment, the medical professional inflates the flexible member 304 to stretch the narrowed urethra 202 by the desired amount, thereby maintaining wound edge separation of the stricture 204. To reduce pressure necrosis, which occurs when wound healing is compromised from a reduced vascular flow, the pressure of the flexible member 304 can be reduced to cause the flexible member 304 to deflate. This reduction in pressure can occur periodically or spontaneously. The medical professional can adjust the controller 336 to decrease the pressure of the flexible member 304, such as via an adjustment of a button on the control panel 340. Alternatively, the controller 336 cycles the pressure supplied to the flexible member 304. This cycling can be based on a software program. For example, the controller 336 can execute a program having instructions to apply a first pressure for 3 seconds, a second pressure for 5 seconds, a third pressure for 10 seconds, and then repeat the previous steps. The medical professional may instead adjust the pressure of the flexible member 304 manually, such as by expanding the opening 316 slightly to let out some air of the flexible member 304. Thus, the cross-sectional area 212 (and therefore diameter) of the flexible member 304 can be adjusted (i.e., increased and/or decreased) at any rate and at any time (e.g., during the implantation of the device and/or during follow-up evaluation of the flexible member 304).

Furthermore, the display screen 344 can display the amount of pressure that the controller 336 supplies through the controller line 348 to the flexible member. The medical professional may also measure the pressure of the flexible member 304 by applying a pressure gauge or monitor to the flexible member 304.

In addition to preventing the reduction of vascular flow, the flexible member 304 also includes a flexible member drainage line 364. In FIG. 3, the flexible member drainage line 364 is a line (or tube) having a portion placed behind the flexible member 304. Thus, the flexible member drainage line 364 enables the drainage of fluids during, for example, the implanting of the flexible member 304. These fluids can be bodily fluids, such as urine and/or blood, that can collect behind, the flexible member 304.

The flexible member drainage line 364 can be made of any material described above. Further, the flexible member drainage line 364 has a drainage port 366 at the proximal end 367 of the flexible member drainage line 364. The drainage port 366 can empty into another location for removal of the bodily fluids and/or waste. For example, the drainage port 366 may empty into a waste container or may connect to a device used to remove or clean the waste.

The flexible member line 320 and the flexible member drainage line 364 can be individually wrapped and/or grouped in a sheath or coating. For example, the sheath or coating can be employed to group the lines 320, 364 together so as to facilitate easy retrieval of each line's contents. Additionally, the flexible member 304 can also be coated to provide additional protection from waste, debris, etc.

The flexible member 304 together with each line 320, 364 and each corresponding connector or port 332, 366 may be referred to below as a flexible member stricture retractor 370. A grouping of the lines 320, 364 in a sheath or coating can also facilitate deploying the flexible member stricture retractor 370 into the patient's urethra 202.

Although described above as being a pneumatic device, the flexible member 304 can also be a hydraulic device. Examples of the fluid that can be used to inflate/deflate the flexible member 304 include saline, sterile water, radiopacifier, and hydrogel. Moreover, a combination of one or more of these fluids can also be used to fill the flexible member 304.

Figure 4:
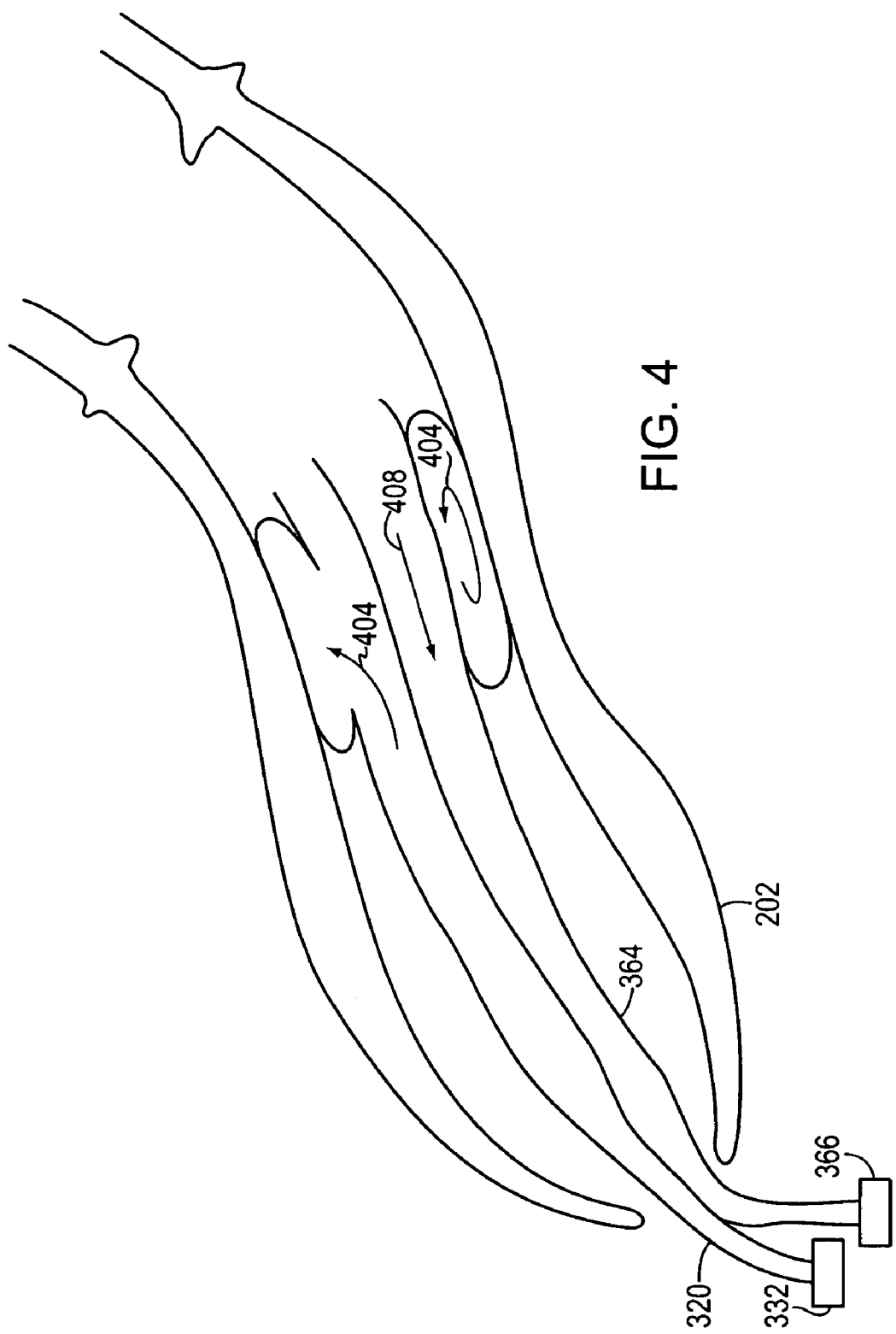
FIG. 4 is a flow diagram of an embodiment of a flexible member stricture retractor inserted into the urethra affected by the stricture.

Referring to FIG. 4, a medical professional inserts the flexible member stricture retractor 370 into the urethra 202. The medical professional can connect the controller 336 to the controller connector 332 and can apply, for example, air (or a liquid) to the flexible member 304, as shown with arrow 404. The flexible member 304 increases in size as the controller 336 applies pressure. Moreover, the flexible member drainage line 364 and the drainage port 366 provide a lumen that enables drainage of the bodily fluids, as shown with arrow 408.

Figure 5:
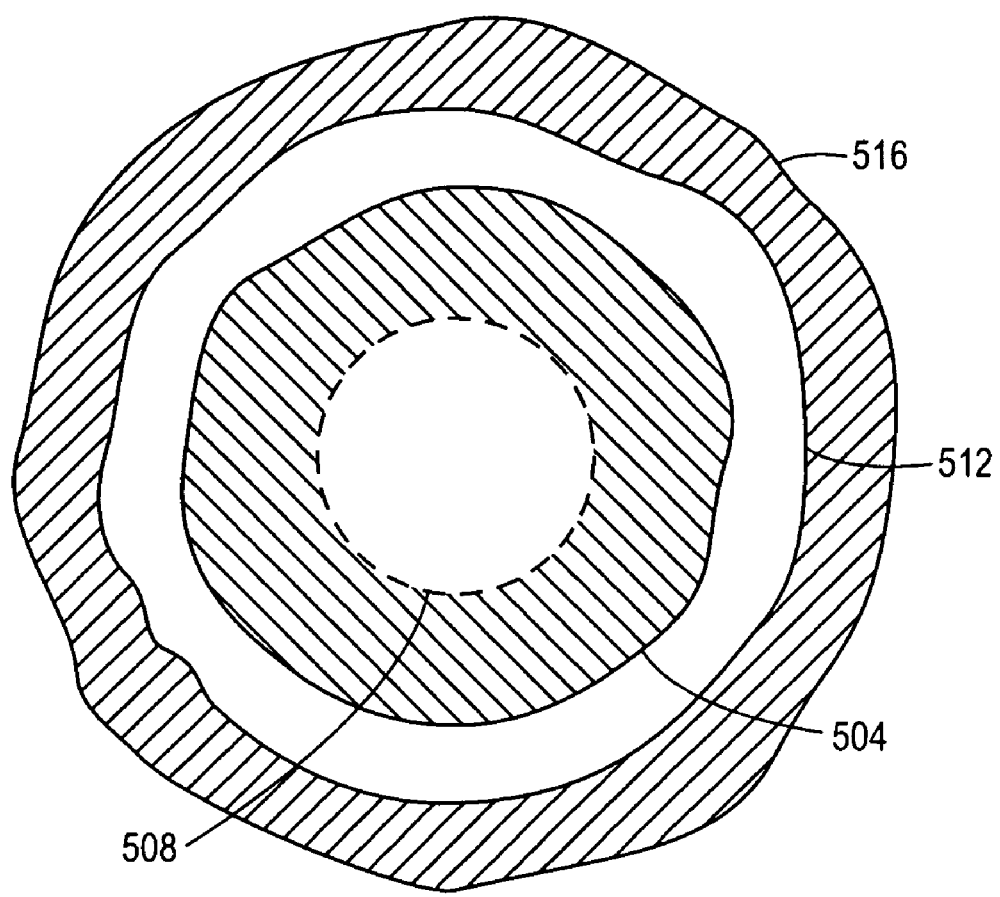
FIG. 5 is an embodiment of a cross-sectional view of a flexible member, stricture, and urethra after the flexible member expands.

Referring to FIG. 5, an embodiment of the cross-section of the stricture 204 and the urethra 202 is shown after the flexible member 304 expands to an expanded cross-sectional area 504 (e.g., in response to the controller's application of pressure). The cross-sectional area of the proximal end 312 of the flexible member 304 is shown as cross-sectional area 508. In particular, the flexible member 304 has opened up the urethra 202 to a cross-sectional area 512 by expanding the stricture 204 to an expanded cross-sectional area 516. Due to this expansion, the stricture 204 no longer substantially narrows the urethra 202.

Figure 6A:
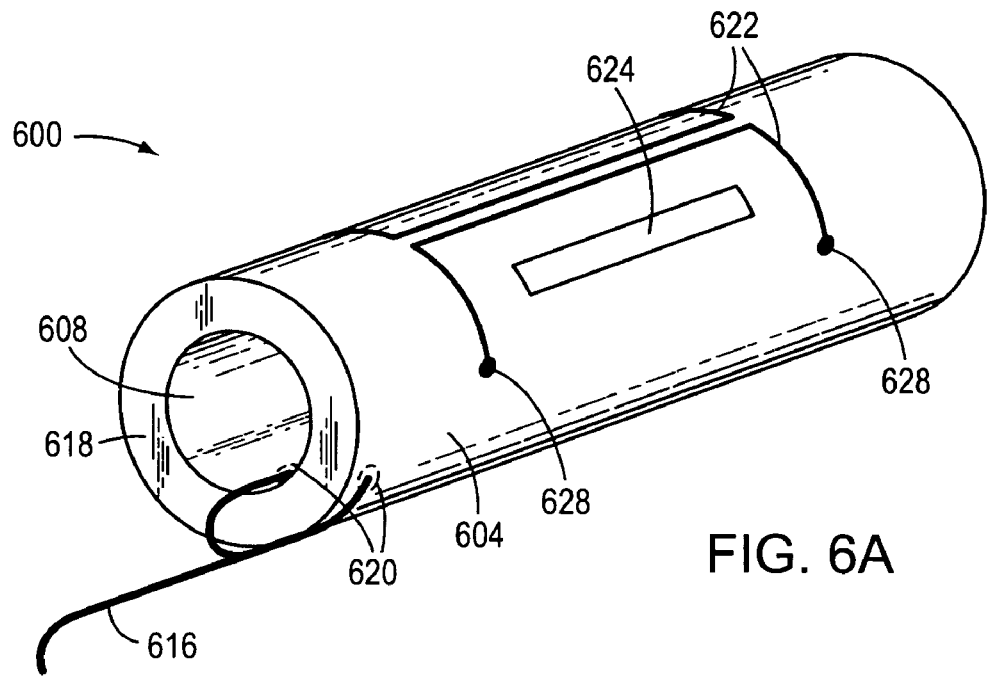
FIG. 6A is an embodiment of a perspective view of an embodiment of a stricture retracting system.
Figure 6B:
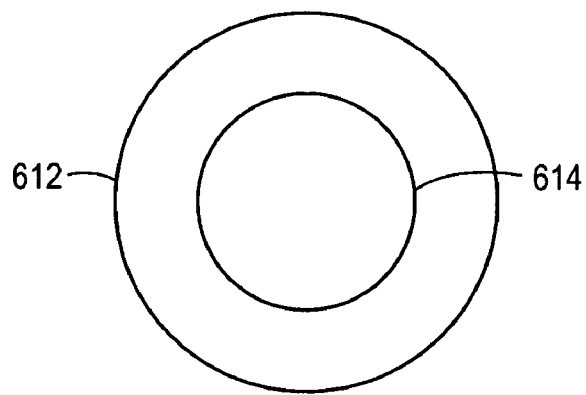
FIG. 6B is an embodiment of a cross-sectional view of the stricture retracting system of FIG. 6A.

Referring to FIGS. 6A and 6B, an alternate stricture retracting system 600 for reducing the wound edges 258 from approximating includes components that can be activated to adjust the cross-sectional area 212 of the urethra 202. The system 600 includes a body 604 that defines a passageway 608. The body 604 is constructed from a circular channel and has an initial cross-sectional area 612. The initial cross-sectional area 612 of the body 604 is less than the cross-sectional area 212 of the affected urethra 202, thereby enabling the insertion of the body 604 into the urethra 202 narrowed by the stricture 204. The passageway 608 has a cross-sectional area 614. Although illustrated as circular, the body 604 and/or the passageway 608 can be any shape or size. Moreover, any part of the stricture retracting system 600 (e.g., the body 604) can be coated with a coating to provide additional protection to the component(s) of the alternate stricture retracting system 600.

The body 604 can additionally be connected to a suture 616. The medical professional can leave the body 604 (or the flexible member 304) in the urethra 202 for a predetermined period of time (e.g., 1-3 days or 7 days) and then use the suture 616 (or lines 320, 364) to retrieve the body 604 from the urethra 202. The suture 616 can have any length needed to enable the retrieval of the body 604. The medical professional can also determine the length of the suture 616 at the time of insertion into the urethra 202, such as by cutting the suture 616. Similarly, the medical professional can connect the suture 616 to the proximal end 618 of the body 604 (e.g., the portion of the body 604 entering the urethra 202 after the other end of the body 604). The connection of the suture 616 can occur by, for example, tying the suture 616 onto the body 604 or taping the suture 616 onto the body. Further, the body 604 can have suture holes 620 for attaching the suture 616 to the body 604. Additionally, the suture 616 can be made from one or more materials, such as nylon.

The body 604 also includes a separating device 622 (shown in an unactivated state in FIG. 6A) disposed relative to the body 604. The separating device 622 is employed to adjust the cross-sectional area 212 of the affected urethra 202 to reduce the approximation of the wound edges 258 of the stricture 204. The separating device 622 can also be coupled to the body 604. The separating device 622 can be coupled to the body 604 via, for instance, mechanical coupling devices (e.g., screws, nails, tape, velcro, glue) or electrical or magnetic coupling techniques (e.g., via one or more magnets or an electrical circuit). Alternatively, the separating device 622 is connected to the body 604. This connection can be via a mechanical linkage, such as one or more tie-rod, link, rope, chain, etc.

The separating device 622 can additionally include a rib 624. The rib 624 may or may not be the same material as the separating device 622 and can be made of, for example, a polymer, plastic, or a combination of materials. The rib 624 can also be any size and shape. Further, although illustrated with one rib 624, the body 604 can include any number of ribs. The rib 624 can protrude from the outside surface of the separating device 622 (or the body 604). The rib 624 can help prevent the body 604 from rotating inside the urethra 202 by, for example, "anchoring" the body 604 into the walls of the urethra 202. Thus, if some type of bodily fluid (e.g., blood) traversing through the urethra 202 provided a torque on the body 604 during the flow of the fluid, the rib 624 can help stabilize the body 604 to facilitate the reduction of wound edge approximation.

Alternatively, the rib 624 is located on the inside of the separating device 622. In this configuration, a medical professional can insert an instrument or item, such as the medical professional's finger, into the passageway 608 defined by the body 604 to activate the rib 624. Activation of the rib 624 can occur by pushing, pulling, or exerting some type of force on the rib 624. The rib 624 can then cause the activation (or deactivation) of the separating device 622 so that the separating device 622 opens or closes.

Furthermore, the separating device 622 can also include stress relief holes 628. The separating device 622 includes stress relief holes 628 to alleviate the stress on the body 604 during activation of the separating device 622, as described in more detail below. The stress relief holes 628 can be any size and shape, and although shown with two stress relief holes 628 in FIG. 6A, the body 604 can have any number of stress relief holes 628.

Figure 7A:
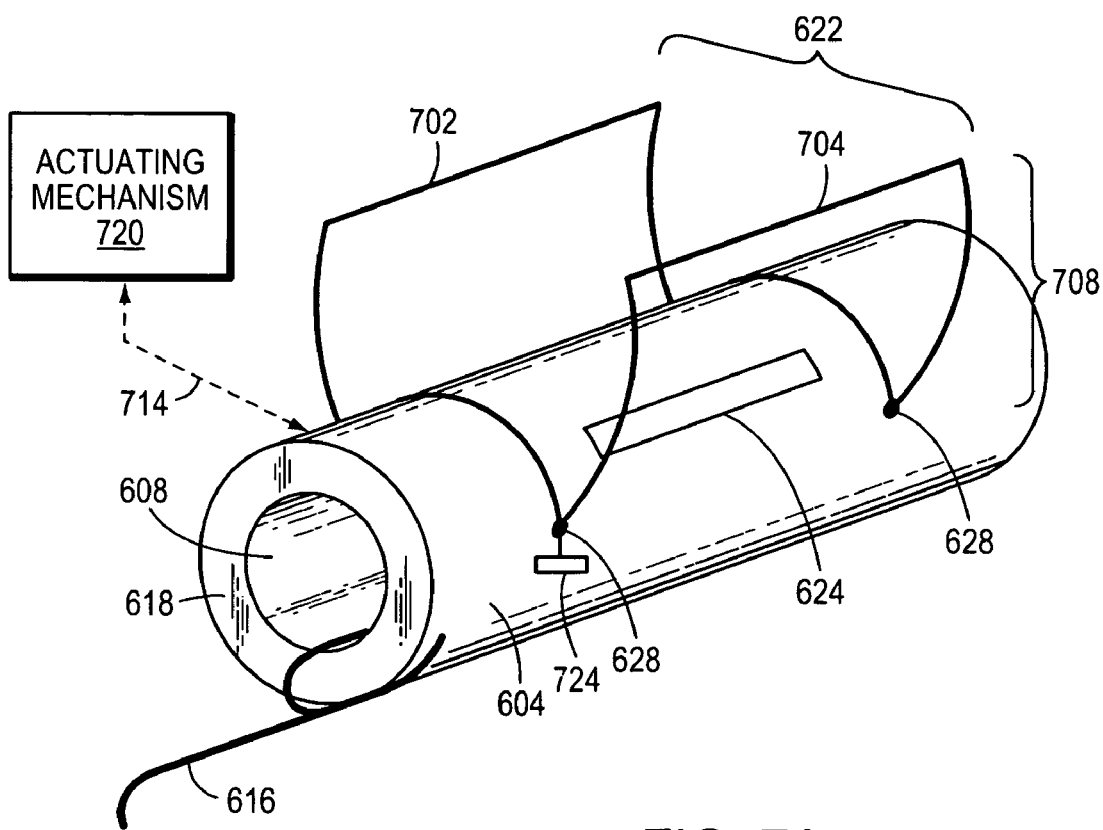
FIG. 7A is a perspective view of another embodiment of the stricture retracting system of FIG. 6A having an actuating mechanism.

Referring to FIG. 7A, the body 604 separates the wound edges 258 of the stricture 204 by activating the separating device 622. The separating device 622 can include a first wing 702 and a second wing 704 that open when activated and close when deactivated. Moreover, the separating device 622 (i.e., the first and/or second wing 702, 704) can open until reaching any angle or until, for instance, blocked from further movement by the body 604. For example, each wing 702, 704 can open 180 degrees relative to its starting position (e.g., 0 degrees) or any angle between 0 and 180 degrees. Although described above and below with two wings 702, 704, the separating device 622 can have any number of wings 702, 704 needed to reduce the approximation of the wound edges 258. Moreover, although the invention is described below with respect to the first wing 702, any application can also be applied to the second wing 704 or both wings 702, 704. Also, the wings 702, 704 are formed from an "I" cut into the body 604.

The separating device 622 additionally has a height 708. Furthermore, different stricture retracting systems 600 can have separating devices 622 with different heights 708. The medical professional can select the height 708 of the separating device 622 before inserting the body 604 into the patient's urethra 202. This determination can be based on, for example, the cross-sectional area 216 of the stricture 204, the cross-sectional area 212 of the urethra 202, and/or the initial cross-sectional area 210 of the unaffected urethra 104. Alternatively, the height 708 of the separating device 622 is adjusted during insertion into the patient's urethra 202, such as by pushing or pulling on the wings 702, 704.

Figure 7B:
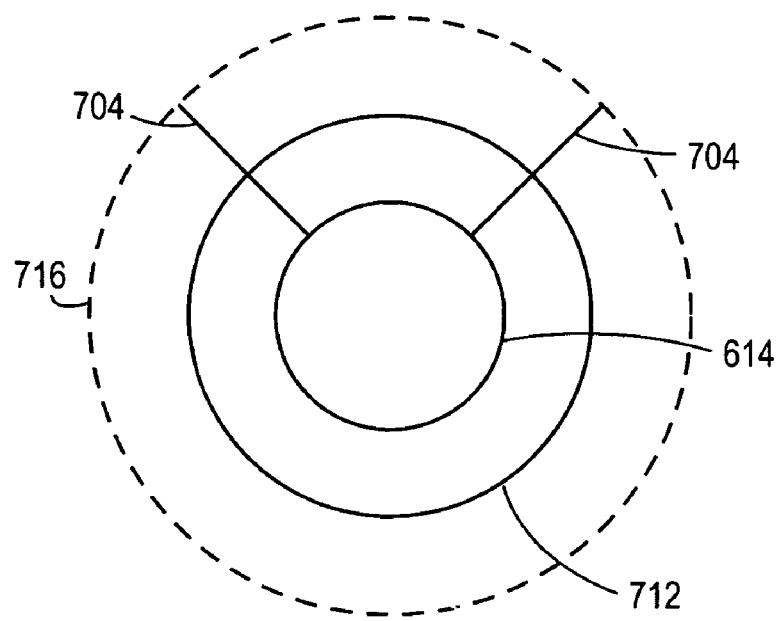
FIG. 7B is an embodiment of a cross-sectional view of the stricture retracting system of FIG. 6A.

Also referring to FIG. 7B, the cross-sectional area 212 of the urethra 202 is adjusted by changing the cross-sectional area 712 of the body 604. As described above, this occurs during the activation of the separating device 622. Upon activation of the separating device 622, the separating device 622 opens to a particular angle and increases the initial cross-sectional area 712 of the body 604 to an expanded, circular cross-sectional area 716. This consequently increases the cross-sectional area 212 of the urethra 202 to reduce the approximation of the wound edges 258. Moreover, the expanded, circular cross-sectional area 716 of the body 604 is derived from and varies depending on the height 708 of the wings 702, 704 of the separating device 622. Additionally, the pressure applied by the wings 702, 704 (i.e., the separating device 622) to the wound edges 258 can vary depending on the amount of narrowing of the urethra 202. Thus, the pressure applied by the separating device 622 can decrease as the urethra 202 "relaxes" and the narrowing of the urethra 202 decreases.

Referring again to FIG. 7A, an actuating mechanism 720 can be used to adjust the separating device 622. The communication between the actuating mechanism 720 and the separating device 622 is shown with arrow 714. The actuating mechanism 720 can additionally wirelessly communicate with the separating device 622. For instance, the actuating mechanism 720 can be a radio frequency (or infrared, microwave, etc.) controller that the medical professional can use to open the separating device 622. The medical professional can also be able to select an angle at which the medical professional prefers to have the actuating mechanism 720 open and inputs this selection into the actuating mechanism 720. The actuating mechanism 720 then adjusts the separating device 622 to open the wings 702, 704 to the selected angle.

The actuating mechanism 720 can mechanically adjust the amount of opening of the separating device 622. The actuating mechanism 720 can be externally located from the body 604 or located within the body 604. In one embodiment, the actuating mechanism 720 connects to an actuating mechanism connector 724. The actuating mechanism connector 724 is an internal component of the body 604 and connected to the separating device 622. Alternatively, the actuating mechanism connector 724 is a component externally located from the body 604, yet still connected to the separating device 622. The actuating mechanism connector 724 can also be a screw. The actuating mechanism 720 can rotate the screw, thereby applying torque to the separating device 622 to open/close the device 622. The actuating mechanism connector 724 can alternatively be a lever. The actuating mechanism 720 can be used to rotate or push the lever in various directions to change the opening amount of the separating device 622.

Although shown with one actuating mechanism connector 724, the body 604 can have any number of actuating mechanism connectors 724 connected to any part of the separating device 622. Moreover, the actuating mechanism connector 724 can be any shape and/or size so long as the connector 724 can adjust the opening of the separating device 622.

The actuating mechanism 720 can be or can communicate with the rib 624. Further, the rib 624 can be located on one or both wings 702, 704. The use of the rib 624 to manually open the separating device 622 can be useful in determining the range of motion of the wings 702, 704, for instance.

Figure 7C:
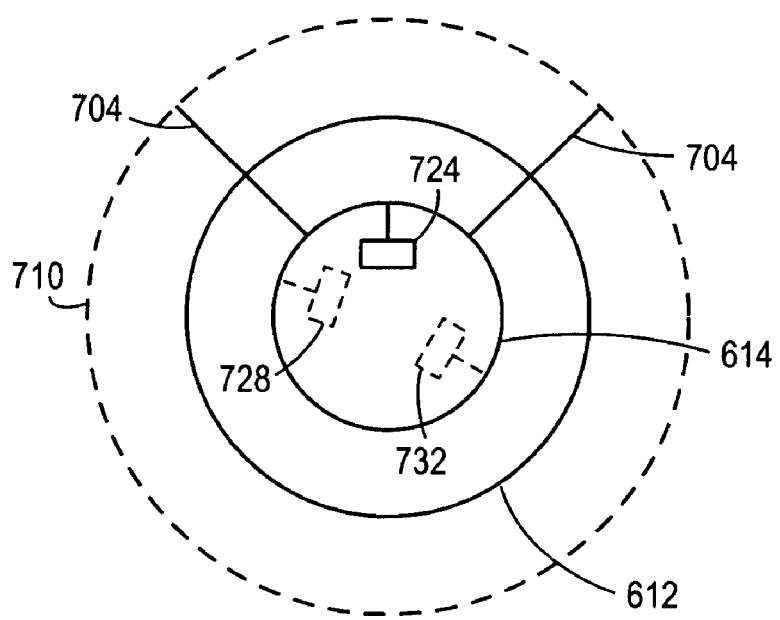
FIG. 7C is an embodiment of a cross-sectional view of the stricture retracting system of FIG. 6A having a connector.

Also referring to FIG. 7C, one end of the actuating mechanism connector 724 can extend from the body 604 into the passageway 608. Additionally, the actuating mechanism connector 724 can be positioned in any configuration. Further, the medical professional can move the actuating mechanism connector 724 to facilitate connection with the actuating mechanism 720. For example, the actuating mechanism connector 724 can be moved to position 728.

Figure 8A:
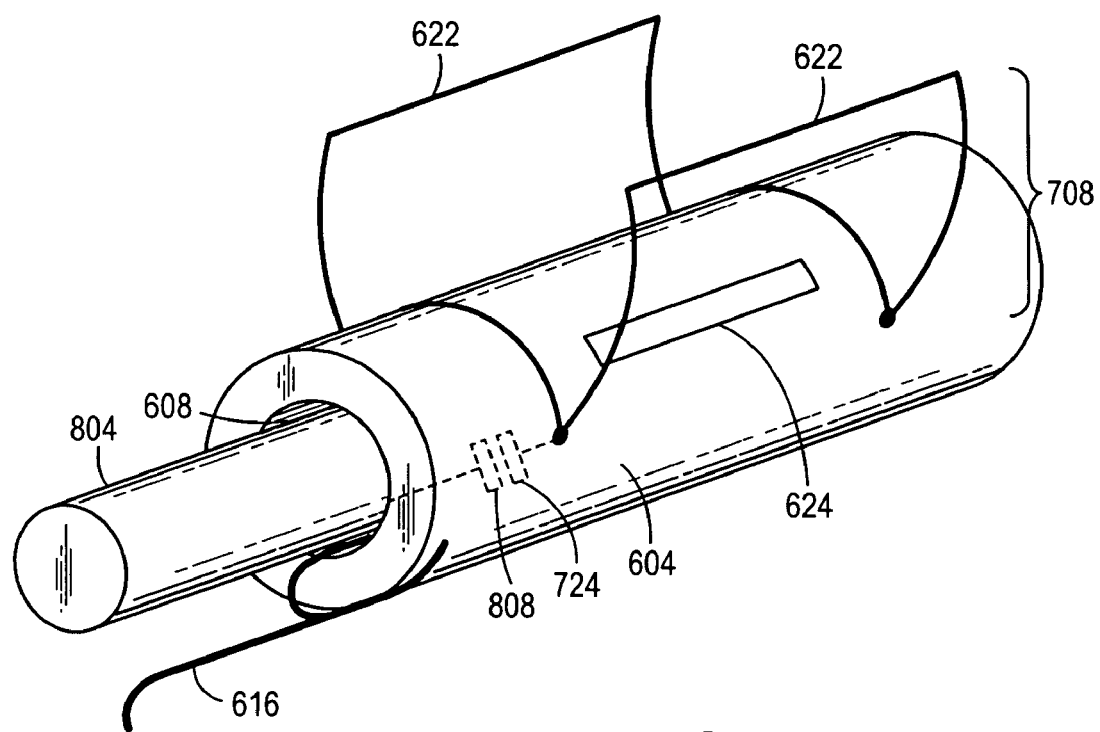
FIG. 8A is a perspective view of an embodiment of the stricture retracting system of FIG. 6A having a cylinder as the actuating mechanism.

Referring to FIG. 8A, the actuating mechanism 720 can be a cylinder 804. The medical professional can insert the cylinder 804 into the passageway 608 defined by the body 604 to adjust the amount of opening of the separating device 622. Further, the medical professional can rotate the cylinder 804 to adjust the amount of opening of the separating device 622. The cylinder 804 can also have a retractable member 808 to connect to the actuating mechanism connector 724. After at least some of the cylinder 804 is inserted into the passageway 608 defined by the body 604, the retractable member 808 can extend out of the cylinder 804 and connect to the actuating mechanism connector 724. In further embodiments, the cylinder 804 is rotated (e.g., by the medical professional, by a magnetic or electrical force, or by an external device such as a controller) to adjust the opening amount of the separating device 622. Moreover, the cylinder 804 can additionally utilize a cam surface to control the amount of opening of the wings 702, 704.

Figure 8B:
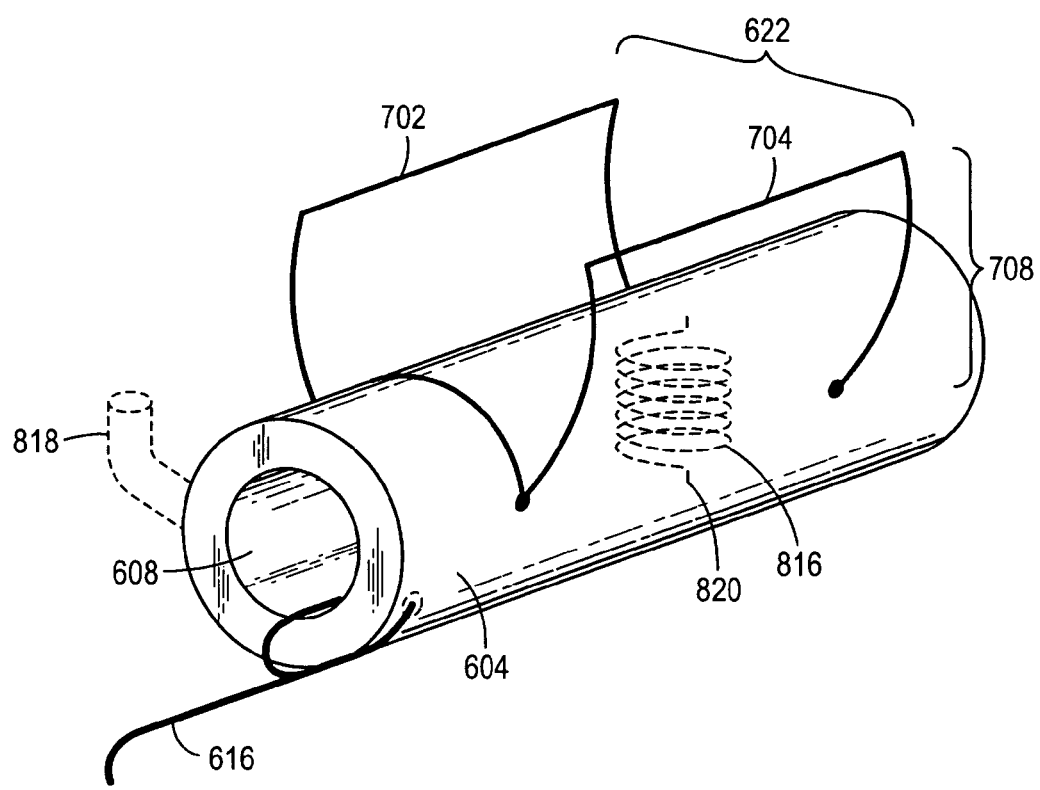
FIG. 8B is perspective view of an embodiment of the stricture retracting system of FIG. 6A having a spring as the actuating mechanism.

Referring to FIG. 8B, the actuating mechanism 720 can also be a spring 816 connected to the separating device 622 (e.g., one of the wings 702, 704). In particular, one end 820 of the spring 816 is secured to the body 604 and the other end of the spring 816 is secured to the separating device 622. Although illustrated with a particular orientation, the spring 816 can be oriented in any fashion to adjust the opening of the separating device 622.

A spring controller 818 can control the amount of extension of the spring 816. In one embodiment, the medical professional adjusts the amount of extension of the spring using the spring controller 818 before inserting the body 604 into the urethra 202. In another embodiment, the medical professional uses the spring controller 818 after inserting the body 604 into the urethra 202 to adjust the spring 816. Although the spring controller 818 is illustrated as a lever, the spring controller 818 can be any type of device having any shape or size.

Figure 8C:
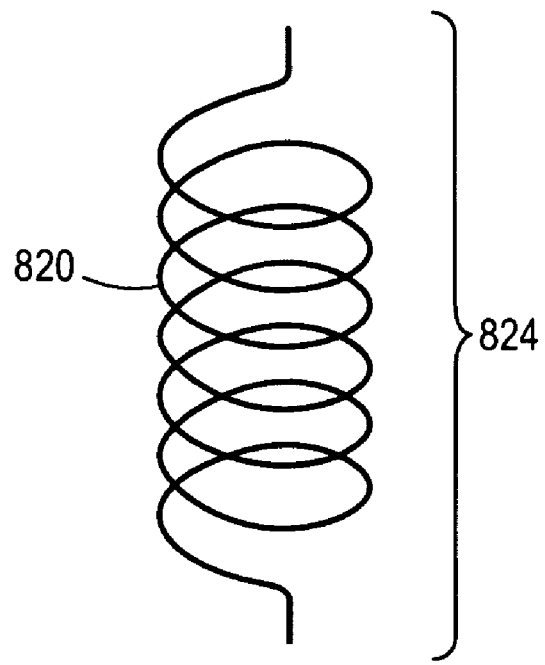
FIG. 8C is a frontal view of the spring of FIG. 8B in a rest state.
Figure 8D:
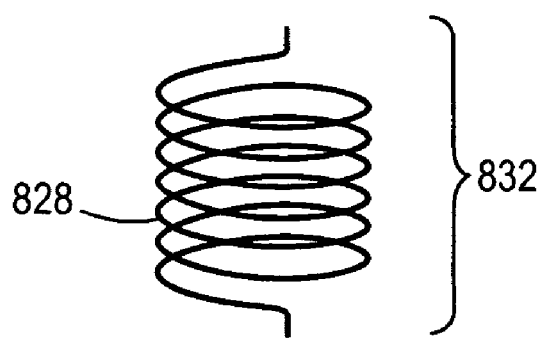
FIG. 8D is a frontal view of the spring of FIG. 8B in a compressed state.

Also referring to FIGS. 8C and 8D, when the spring 816 is in a rest or unrestrained state in which no external forces are exerted upon any portion of the spring 816, the spring 816 becomes an unrestrained spring 820 having an initial length 824. In one embodiment, the unrestrained spring 820, when secured to the body 604 and the wing 702, 704, maintains the wing 702, 704 in a partly-opened position. The unrestrained spring 820 can alternatively maintain the wing 702, 704 in a fully opened position. When inserting the separating device 622 into the urethra 202, the medical professional may compress the unrestrained spring 820 to a compressed state (i.e., compressed spring 828). The compressed spring 828 has a height 832 that is less than the height 824 of the unrestrained spring 820. The spring 816 can additionally have a spring spread of (i.e., can be stretched or extended) substantially greater than or equal to two times the thickness of the incision cut 220.

Figure 9:
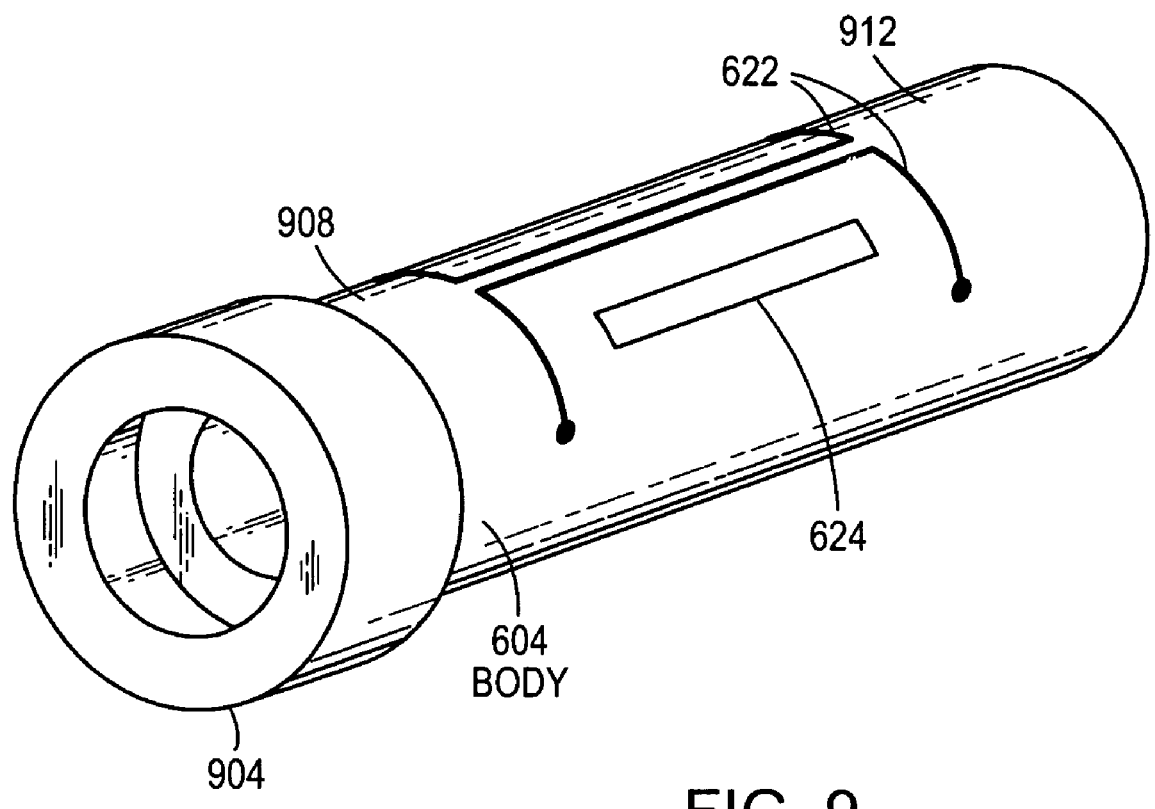
FIG. 9 is a perspective view of an embodiment of the stricture retracting system of FIG. 6A having a control ring.

Referring to FIG. 9, the body 604 can also include a control ring 904. A medical professional may slide the control ring 904 along the body 604 to adjust the stability of the body 604. Thus, the control ring 904 can provide additional traction to the body 604 so that the body 604 remains in its desired position while, for instance, bodily fluids rush through the passageway 608. Therefore, the medical professional may slide the control ring 904 to position 908 to provide additional stability to the body 604 at that location. The medical professional may also slide the control ring 904 to position 912 for increased stability. The control ring 904 can be any thickness and any length. Moreover, the control ring 904 can be made of any material, such as thermoplastic. Although illustrated as a ring, the control ring 904 can be a tube or other structure which is moveable along the body 604. The control ring 904 can be moved to any position along the body 604.

Figure 10:
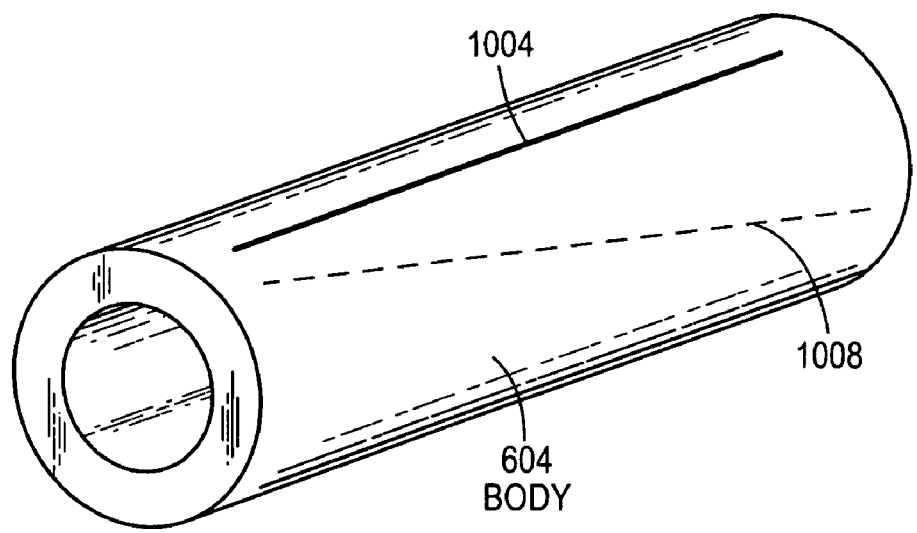
FIG. 10 is a perspective view of an embodiment of the stricture retracting system of FIG. 6A having slits in various positions.

Referring to FIG. 10 and instead of the "I" cut that forms the wings 702, 704 in the body 604, the body 604 can have a slit cut into it. The slit can be an axial slit 1004 cut along the axis of the body 604. In other embodiments, the slit can be an angled slit 1008. These slits 1004, 1008 can provide additional flexibility to the body 604. Further, upon activation through any of the means described above, the slit 1004, 1008 can open, creating wings (e.g., long or unsymmetrical) which can reduce wound edge approximation.

Figure 11:
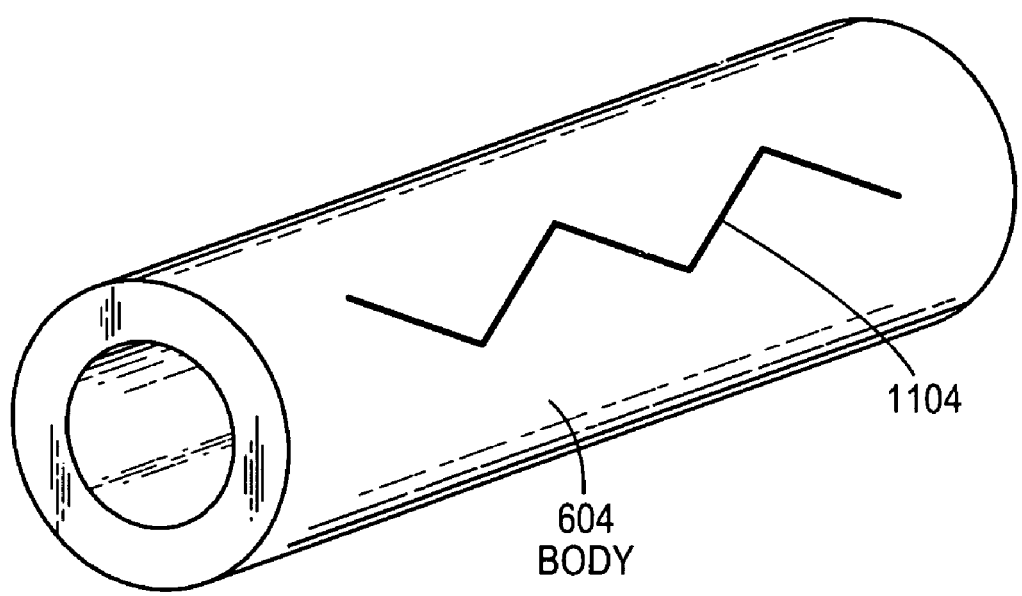
FIG. 11 is a perspective view of an embodiment of the stricture retracting system of FIG. 6A having a zig-zag slit.

Referring to FIG. 11, the body 604 can alternatively have any type of slit creating wings of any shape. The medical professional may desire wings having different shapes depending on the patient, the patient's urethra 202, the desired flexibility of the stricture retracting system 600, the ease at which the body 604 can fit inside the urethra 202, etc. For example, the body 604 can have a zig-zag slit 1104 to facilitate any of the previously mentioned purposes (e.g., increase the body's flexibility).

Figure 12:
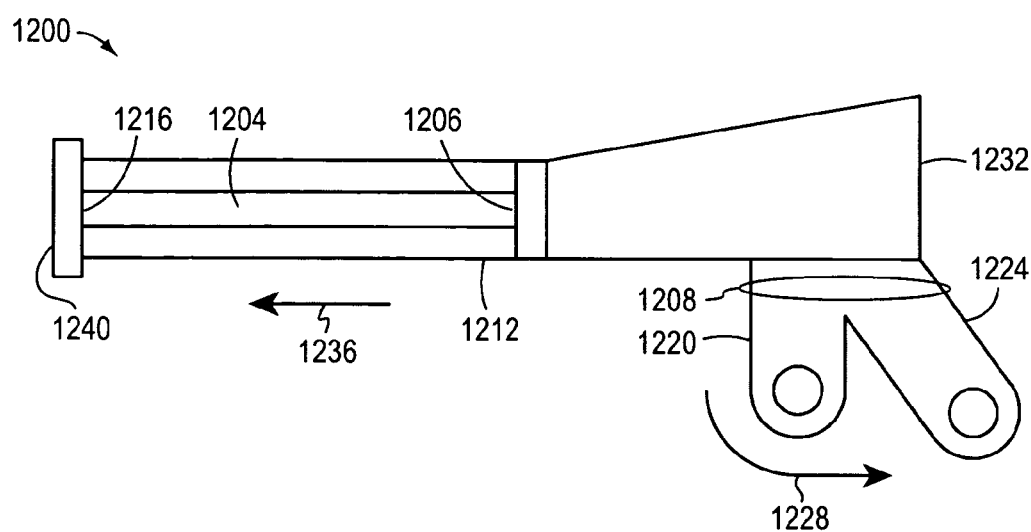
FIG. 12 is a block diagram of an embodiment of a stricture retractor delivery system.

Referring to FIG. 12, the medical professional uses a stricture retractor delivery system 1200 to deploy flexible member stricture retractor 370 or the stricture retracting system 600 (e.g., the body 604, the separating device 622, the suture 616, etc.). The stricture retractor delivery system 1200 can include a sliding member 1204 to exert a deploying force on the proximal end 328, 367 (or controller connector 332 or drainage port 366) of the lines 320, 364, respectively. Similarly, the sliding member 1204 of the stricture retractor delivery system 1200 can provide a deploying force on the proximal end 618 of the body 604.

Additionally, the proximal end 1206 of the stricture retractor delivery system 1200 can include a handle 1208. The handle 1208 enables the sliding member 1204 to slide along a body 1212 of the stricture retractor delivery system 1200. In particular, the handle 1208 can be coupled to the sliding member 1204. The medical professional uses the handle 1208 to slide the sliding member 1204 along the body 1212 to exert the deploying force. In particular, the medical professional causes the sliding member 1204 to slide towards the distal end 1216 of the stricture retractor delivery system 1200 by pulling an inside handle arm 1220 towards an outside handle arm 1224 (shown by arrow 1228).

The handle 1208 can also include a spring attached from the proximal end 1232 of the stricture retractor delivery system 1200 to the proximal end 1206 of the sliding member 1204. The handle 1208 includes the spring so that the movement of the inside handle arm 1220 towards the outside handle arm 1224 compresses the spring. Upon release of the handle arms 1220, 1224, the spring subsequently expands longitudinally to provide an actuation force on the sliding member 1204. The actuation force produces movement of the sliding member 1204 along line 1236 so that the sliding member 1204 can exert the deploying force on, for example, the proximal end 618 of the body 604. Any other means can also be used to provide an actuation force on and subsequent movement of the sliding member 1204.

In one embodiment, the device that the stricture retractor delivery system 1200 is deploying (e.g., the flexible member stricture retractor 370 or the alternate stricture retracting system 600) fits inside the body 1212 of the stricture retractor delivery system 1200. In this deployment technique, the sliding member 1204 is pushed (either manually or via pushing the inside handle arm 1220 towards the outside handle arm 1224) into the body 1212 so that the sliding member 1204 contacts a part of (e.g., controller connector 332, drainage port 366, or proximal end 618) the device (e.g., flexible member stricture retractor 370 or alternate stricture retracting system 600) to be deployed.

Further, the sliding member 1204 can include a deploying mechanism 1240 attached to its distal end 1216 to ensure that the sliding member 1204 provides the deploying force on, for instance, the body 604 and does not extend into the passageway 608 of the body 604 without making contact with the body 604. The deploying mechanism 1240 can be a circular-shaped member in which a portion contacts the proximal end 618 of the body 604 as a result of the movement of the sliding member 1204 from the actuation force. Alternatively, the deploying mechanism 1304 can be any shaped mechanism, such as square, octagonal, and triangular, so long as the sliding member 1304 provides some sort of deploying force on the body 604 to deploy the body 604 into the patient's urethra 202. Although described above as being deployed by the stricture retractor delivery system 1200, the flexible member stricture retractor 370 and/or the stricture retracting system 600 can be deployed by any delivery device or technique.

In another embodiment, the device that the stricture retractor delivery system 1200 is deploying is located beyond the stricture retractor delivery system 1200, but the actuating of the sliding member 1204 extends the sliding member 1204 beyond the stricture retractor delivery system 1200 so that the sliding member 1204 still provides the deploying force. In this embodiment, the device being deployed can only be up to a particular distance away from the stricture retractor delivery system 1200 so that the sliding member 1204 extends far enough to make contact with and provide the deploying force to the device.

Having described certain embodiments of the invention, it will now become apparent to one of skill in the art that other embodiments incorporating the concepts of the invention can be used. Therefore, the invention should not be limited to certain embodiments, but rather should be limited only by the spirit and scope of the following claims.

What is claimed is:

1. A system for reducing approximation of a plurality of wound edges of a stricture that affects a cross-sectional area of a lumen in a mammal, the system comprising:
    a body defining a passageway for fluid flow and positionable in the lumen;
    a separating device disposed relative to the body for adjusting the cross-sectional area of the lumen, the separating device including a first wing, a second wing, and at least one rib disposed on an inside surface of at least one of the first and second wing, the first wing being configured to rotate about a first axis in a first direction to move from a collapsed configuration to an expanded configuration, the second wing configured to rotate about a second axis in a second direction to move from a collapsed configuration to an expanded configuration, the first axis and the second axis being substantially parallel to the passageway, the first direction different from the second direction, and
    an actuating mechanism in communication with the at least one rib to adjust the amount of opening of the first wing or the second wing.

2. The system of claim 1 wherein the separating device is connected to the body.

3. The system of claim 1 wherein the separating device is coupled to the body.

4. The system of claim 1 wherein the actuating mechanism further comprises a spring operatively connected to the first wing.

5. The system of claim 1 wherein the actuating mechanism further comprises at least one mechanical device, a pneumatic device, a hydraulic device, and an electronic device.

6. The system of claim 1 wherein the actuating mechanism further comprises a slide cam operatively connected to the first wing.

7. The system of claim 1 wherein the actuating mechanism further comprises a screw cam connected to the first wing to dispose the first wing in its collapsed configuration and its expanded configuration.

8. The system of claim 1 wherein the body further comprises a control ring enabling adjustment of the cross-sectional area of the lumen.

9. The system of claim 1 wherein the first wing and the second wing are formed from an "I" cut in the body.

10. The system of claim 1 wherein the first wing has a length when in the collapsed configuration and a length when in the expanded configuration, the length of the first wing when the first wing is in its expanded configuration is substantially the same as the length of the first wing when the first wing is in its collapsed configuration.

11. The system of claim 1 wherein the first wing is substantially solid.

12. The system of claim 1 wherein the actuating mechanism is configured to selectively retain the first wing in its collapsed configuration and in its expanded configuration.

13. The system of claim 1 wherein the first wing is disposed at a first angle with respect to the body when in its collapsed configuration and at a second angle with respect to the body when in its expanded configuration, the second angle being greater than the first angle.

14. The system of claim 1 wherein a distal end of the first wing is disposed a first distance from the body when the first wing is in its collapsed configuration and a second distance from the body when the first wing is in its expanded configuration, the second distance being greater than first distance.

15. The system of claim 1 wherein the system is configured to be inserted into a lumen of a mammal when the first wing and the second wing are in their collapsed configurations and is configured to expand the cross-section of the lumen when the first wing and the second wing are in their expanded configurations.

16. The system of claim 1 wherein the system has a first cross-sectional area when the first wing and the second wing are in their collapsed configurations and a second cross-sectional area when the first wing and the second wing are in their expanded configurations, the second cross-sectional area being greater than the first cross-sectional area.

17. The system of claim 1 wherein the first wing and the second wing are configured to rotate to reach any angle or until blocked from further movement by the lumen in the mammal.

18. The system of claim 1 wherein the first direction is opposite the second direction.

19. A system for reducing approximation of wound edges of a stricture that affects a cross-sectional area of a lumen in a mammal, the system comprising:

a first wing means and a second wing means capable of rotational deployment from a collapsed configuration to an expanded configuration for adjusting the cross-sectional area of the lumen to reduce approximation of the wound edges of the stricture, the first wing means being configured to rotate about a first axis in a first direction, the second wing means having being configured to rotate about a second axis in a second direction, the first direction being different from the second direction;

means for facilitating fluid flow through the lumen after adjusting the cross-sectional area of the lumen, said facilitating means comprising a passageway for fluid flow, wherein the axes of rotation for the first wing means and the second wing means are substantially parallel to the passageway, and means for adjusting the amount of opening of the first wing means and the second wing means, the means for adjusting the amount of opening including at least one rib disposed on an inside surface of at least one of the first and second wing means.

20. The system of claim 19 further comprising means for varying pressure to adjust the cross-sectional area of the lumen.

21. The system of claim 19 further comprising means for varying pressure to facilitate the fluid flow through the lumen.

22. The system of claim 19 wherein the system is configured to be inserted into a lumen of a mammal when the first wing means and the second wing means are in their collapsed configurations and is configured to expand the cross-section of the lumen when the first wing and the second wing are in their expanded configurations.

23. The system of claim 19 wherein the system has a first cross-sectional area when the first wing and the second wing are in their collapsed configurations and a second cross-sectional area when the first wing means and the second wing means are in their expanded configurations, the second cross-sectional area being greater than the first cross-sectional area.

24. The system of claim 19 wherein the first direction is opposite the second direction.

* * * * *